United States Patent
Abrahamson et al.

(10) Patent No.: US 7,871,612 B2
(45) Date of Patent: *Jan. 18, 2011

(54) METHODS OF USE OF SIALOADHESIN FACTOR-2 ANTIBODIES

(75) Inventors: Julie A. Abrahamson, Harlow (GB); Connie L Erickson-Miller, King of Prussia, PA (US); Kristine K. Kikly, Fortville, IN (US); Bruce Bochner, Lutherville, MD (US); Robert Schleimer, Baltimore, MD (US); T. Esra Nutku, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 792 days.

This patent is subject to a terminal disclaimer.

(21) Appl. No.: 11/546,586

(22) Filed: Oct. 12, 2006

(65) Prior Publication Data

US 2008/0213212 A1     Sep. 4, 2008

Related U.S. Application Data

(60) Division of application No. 10/232,187, filed on Aug. 29, 2002, now abandoned, which is a continuation-in-part of application No. PCT/US01/07193, filed on Mar. 5, 2001.

(60) Provisional application No. 60/187,595, filed on Mar. 7, 2000, provisional application No. 60/315,943, filed on Aug. 30, 2001, provisional application No. 60/349,830, filed on Jan. 18, 2002, provisional application No. 60/394,741, filed on Jul. 10, 2002.

(51) Int. Cl.
*A61K 39/395* (2006.01)

(52) U.S. Cl. .................................. 424/130.1

(58) Field of Classification Search ........................ None
See application file for complete search history.

(56) References Cited

U.S. PATENT DOCUMENTS

| 5,834,423 | A | 11/1998 | Koketsu et al. |
| 6,146,845 | A | 11/2000 | Kikly et al. |
| 7,557,191 | B2 * | 7/2009 | Abrahamson et al. .... 530/387.1 |
| 2010/0056760 | A1 * | 3/2010 | Abrahamson et al. .... 530/387.3 |

FOREIGN PATENT DOCUMENTS

| JP | 11028095 A | 2/1999 |
| WO | WO 97/43416 | 11/1997 |
| WO | WO 00/44777 | 8/2000 |

OTHER PUBLICATIONS

Blazer et al., J. Immunol., 1996, 157: 3250-3259.*
von Gunten et al., 2007, J. Allergy Clin. Immunol., 119: 1005-1011 (provided by Applicant).*
Nutku et al., 2003, Blood, 101: 5014-5020 (provided by Applicant).*
Song et al., 2009, Clin. Immunol., 131: 157-169.*
Song et al., 2009, J. Immunol., 183: 5333-5341.*
The International Search cited in PCT/US0107193.
Duarte et al., "Multiepitope Polypeptide of the HIV-1 Envelope Induces Neutralizing Monoclonal Antibodies Against V3 Loop", AIDS Research and Human Retroviruses, NY, NY, vol. 10, No. 3, pp. 235-243, (1994).
Floyd, et al., "Siglec-8: A Novel Eosinophil-Specific Member of the Immunoglobulin Super Family" *The Journal of Biological Chemistry*, vol. 275, No. 2, pp. 861-866 (Jan. 14, 2000).
Foussias, et al., "Molecular Characterization of a Siglec-8 Variant Containing Cytoplasmic Tyrosine-Based Motifs and Mapping of the Siglec-8 Gene" *Biochem Biophys. Res. Commun.* vol. 278, pp. 775-781 (Nov. 2000).
Rudikoff et al., Proc. Natl. Acad. Sci., USA, vol. 72, pp. 1979-1983, (1982).

* cited by examiner

*Primary Examiner*—Ilia Ouspenski
(74) *Attorney, Agent, or Firm*—Edwards Angell Palmer & Dodge LLP; Peter F. Corless; Melissa Hunter-Easor, Esq.

(57) ABSTRACT

Monoclonal antibodies have been generated that bind to human sialoadhesion factor-2. These antibodies are useful as diagnostic and therapeutic reagents.

10 Claims, 8 Drawing Sheets

```
         1 0                                       30
   Q   V   Q   L   K   E   S   G   P   G   L   V   A   P   S
  CAG GTT CAG CTA AAG GAG TCA GGA CCT GGC CTG GTG GCG CCC TCA
  GTC CAA GTC GAT TTC CTC AGT CCT GGA CCG GAC CAC CGC GGG AGT
         50                        7 0                     90
   Q   S   L   S   I   T   C   T   V   S   G   F   S   L   T
  CAG AGC CTG TCC ATC ACT TGC ACT GTC TCT GGG TTT TCA TTA ACC
  GTC TCG GAC AGG TAG TGA ACG TGA CAG AGA CCC AAA AGT AAT TGG
                        1 10                       13 0
   I   Y   G   A   H   W   V   R   Q   P   P   G   K   G   L
  ATC TAT GGT GCA CAC TGG GTT CGC CAG CCT CCA GGA AAG GGT CTG
  TAG ATA CCA CGT GTG ACC CAA GCG GTC GGA GGT CCT TTC CCA GAC
                       150                        1 70
   E   W   L   G   V   I   W   A   G   G   S   T   N   Y   N
  GAG TGG CTG GGA GTA ATA TGG GCT GGT GGA AGC ACA AAT TAT AAT
  CTC ACC GAC CCT CAT TAT ACC CGA CCA CCT TCG TGT TTA ATA TTA
                 19 0                         210
   S   A   L   M   S   R   L   S   I   S   K   D   N   S   K
  TCG GCT CTC ATG TCC AGA CTG AGC ATC AGC AAA GAC AAC TCC AAG
  AGC CGA GAG TAC AGG TCT GAC TCG TAG TCG TTT CTG TTG AGG TTC
         2 30                     25 0                    270
   S   Q   V   F   L   K   I   N   S   L   Q   T   D   D   T
  AGC CAA GTT TTC TTA AAA ATA AAC AGT CTG CAA ACT GAT GAC ACA
  TCG GTT CAA AAG AAT TTT TAT TTG TCA GAC GTT TGA CTA CTG TGT
                        2 90                      31 0
   A   L   Y   Y   C   A   R   D   G   S   S   P   Y   Y   Y
  GCC CTG TAC TAC TGT GCC AGA GAC GGT AGT AGC CCC TAT TAC TAT
  CGG GAC ATG ATG ACA CGG TCT CTG CCA TCA TCG GGG ATA ATG ATA
                       330                         3 50
   S   M   E   Y   W   G   Q   G   T   S   V   T   V   S   S
  TCT ATG GAA TAC TGG GGT CAA GGA ACC TCA GTC ACC GTC TCC TCA
  AGA TAC CTT ATG ACC CCA GTT CCT TGG AGT CAG TGG CAG AGG AGT
```

```
         1 0                              30
 E   I   I   L   T   Q   S   P   A   I   M   S   A   S   P
GAG ATA ATC CTG ACC CAG TCT CCA GCA ATC ATG TCT GCA TCT CCA
CTC TAT TAG GAC TGG GTC AGA GGT CGT TAG TAC AGA CGT AGA GGT
        50                      7 0                      90
 G   E   K   V   S   I   T   C   S   A   T   S   S   V   S
GGG GAG AAG GTC TCC ATA ACC TGC AGT GCC ACC TCA AGT GTA AGT
CCC CTC TTC CAG AGG TAT TGG ACG TCA CGG TGG AGT TCA CAT TCA
                        1 10                     13 0
 Y   M   H   W   F   Q   Q   K   P   G   T   S   P   K   L
TAC ATG CAC TGG TTC CAG CAG AAG CCA GGC ACT TCT CCC AAA CTC
ATG TAC GTG ACC AAG GTC GTC TTC GGT CCG TGA AGA GGG TTT GAG
                150                             1 70
 W   I   Y   S   T   S   N   L   A   S   G   V   P   V   R
TGG ATT TAT AGC ACA TCC AAC CTG GCT TCT GGA GTC CCT GTT CGC
ACC TAA ATA TCG TGT AGG TTG GAC CGA AGA CCT CAG GGA CAA GCG
                        19 0                     210
 F   S   G   S   G   S   G   T   S   Y   S   L   T   I   S
TTC AGT GGC AGT GGA TCT GGG ACC TCT TAC TCT CTC ACA ATC AGC
AAG TCA CCG TCA CCT AGA CCC TGG AGA ATG AGA GAG TGT TAG TCG
        2 30                            25 0                     270
 R   M   E   A   E   D   A   A   T   Y   Y   C   Q   Q   R
CGA ATG GAG GCT GAA GAT GCT GCC ACT TAT TAC TGC CAG CAA AGG
GCT TAC CTC CGA CTT CTA CGA CGG TGA ATA ATG ACG GTC GTT TCC
                        2 90                     31 0
 S   S   Y   P   F   T   F   G   S   G   T   K   L   E   I
AGT AGT TAC CCA TTC ACG TTC GGC TCG GGG ACA AAG TTG GAA ATA
TCA TCA ATG GGT AAG TGC AAG CCG AGC CCC TGT TTC AAC CTT TAT

K   R
AAA CGG
TTT GCC
```

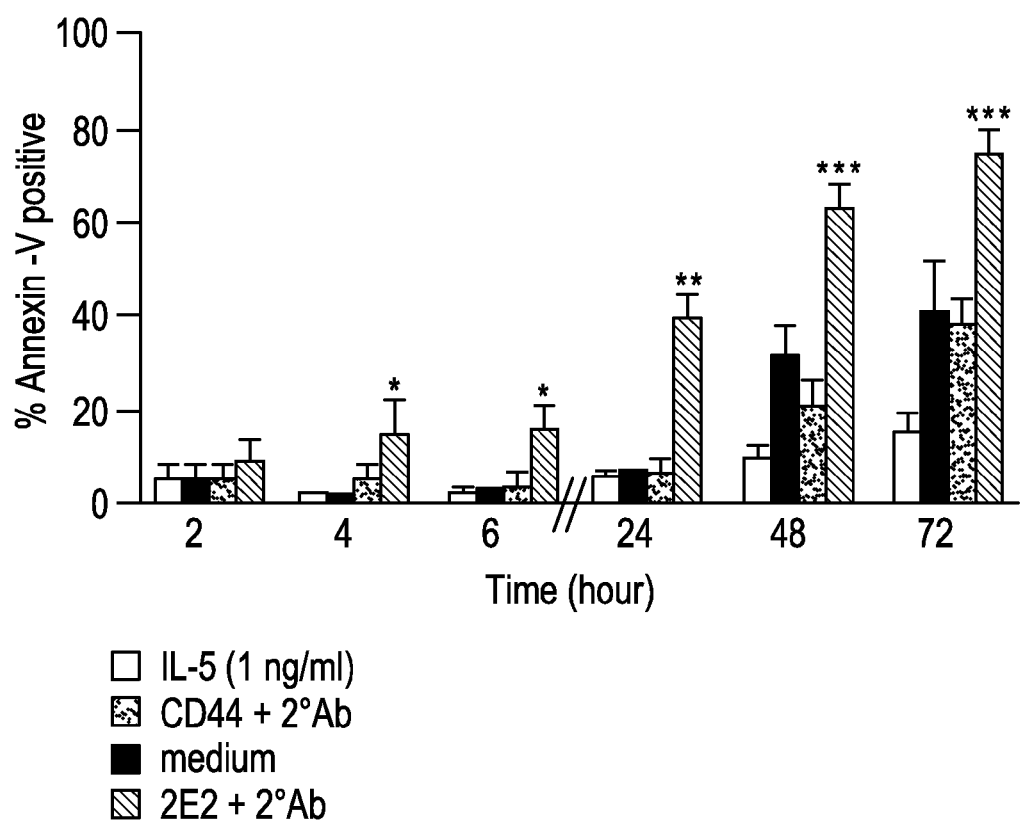

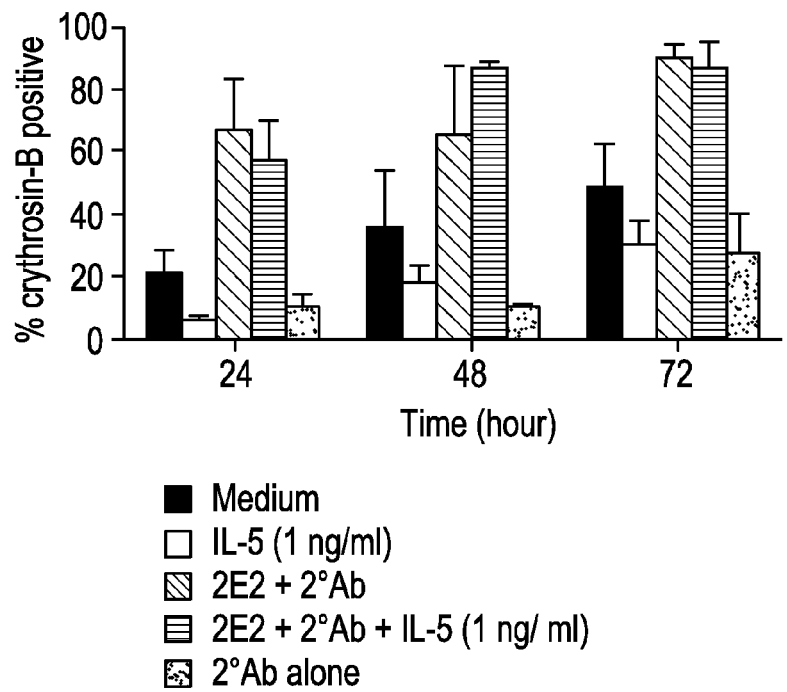
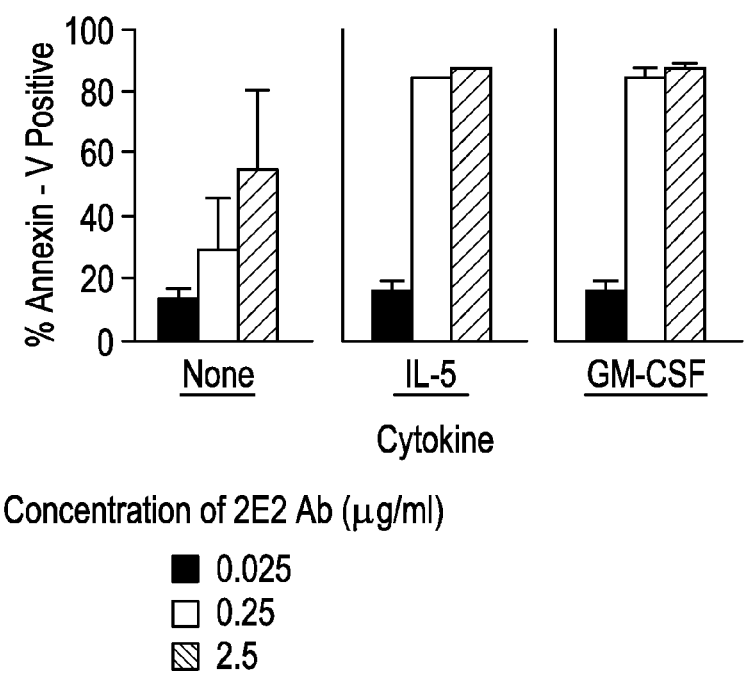

SEQUENCE LISTING

```
<160> NUMBER OF SEQ ID NOS: 14

<210> SEQ ID NO 1
<211> LENGTH: 360
<212> TYPE: DNA
<213> ORGANISM: Homo sapien

<400> SEQUENCE: 1
caggttcagc taaaggagtc aggacctggc ctggtggcgc cctcacagag cctgtccatc      60
acttgcactg tctctgggtt ttcattaacc atctatggtg cacactgggt tcgccagcct     120
ccaggaaagg gtctggagtg gctgggagta atatgggctg gtggaagcac aaattataat     180
tcggctctca tgtccagact gagcatcagc aaagacaact ccaagagcca agttttctta     240
aaaataaaca gtctgcaaac tgatgacaca gccctgtact actgtgccag agacggtagt     300
agcccctatt actattctat ggaatactgg ggtcaaggaa cctcagtcac cgtctcctca     360

<210> SEQ ID NO 2
<211> LENGTH: 119
<212> TYPE: PRT
<213> ORGANISM: Homo sapien

<400> SEQUENCE: 2

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ile Tyr Gly
            20                  25                  30
```

```
Ala His Trp Val Arg Gln Pro Pro Gly Lys Gly Leu Glu Trp Leu Gly
        35                  40                  45
Val Ile Trp Ala Gly Gly Ser Thr Asn Tyr Asn Ser Ala Leu Met Ser
 50                  55                  60
Arg Leu Ser Ile Ser Lys Asp Asn Ser Lys Ser Gln Val Phe Leu Lys
 65                  70                  75                  80
Ile Asn Ser Leu Gln Thr Asp Asp Thr Ala Leu Tyr Tyr Cys Ala Arg
                 85                  90                  95
Asp Gly Ser Ser Pro Tyr Tyr Tyr Ser Met Glu Tyr Trp Gly Gln Gly
                100                 105                 110
Thr Ser Val Thr Val Ser Ser
        115
```

```
<210> SEQ ID NO 3
<211> LENGTH: 321
<212> TYPE: DNA
<213> ORGANISM: Homo sapien

<400> SEQUENCE: 3
gagataatcc tgacccagtc tccagcaatc atgtctgcat ctccagggga gaaggtctcc      60
ataacctgca gtgccacctc aagtgtaagt tacatgcact ggttccagca gaagccaggc     120
acttctccca aactctggat ttatagcaca tccaacctgg cttctggagt ccctgttcgc     180
ttcagtggca gtggatctgg gacctcttac tctctcacaa tcagccgaat ggaggctgaa     240
gatgctgcca cttattactg ccagcaaagg agtagttacc cattcacgtt cggctcgggg     300
acaaagttgg aaataaaacg g                                               321
```

```
<210> SEQ ID NO 4
<211> LENGTH: 107
<212> TYPE: PRT
<213> ORGANISM: Homo sapien

<400> SEQUENCE: 4

Glu Ile Ile Leu Thr Gln Ser Pro Ala Ile Met Ser Ala Ser Pro Gly
  1               5                  10                  15
Glu Lys Val Ser Ile Thr Cys Ser Ala Thr Ser Ser Val Ser Tyr Met
                 20                  25                  30
His Trp Phe Gln Gln Lys Pro Gly Thr Ser Pro Lys Leu Trp Ile Tyr
         35                  40                  45
Ser Thr Ser Asn Leu Ala Ser Gly Val Pro Val Arg Phe Ser Gly Ser
 50                  55                  60
Gly Ser Gly Thr Ser Tyr Ser Leu Thr Ile Ser Arg Met Glu Ala Glu
 65                  70                  75                  80
Asp Ala Ala Thr Tyr Tyr Cys Gln Gln Arg Ser Ser Tyr Pro Phe Thr
                 85                  90                  95
Phe Gly Ser Gly Thr Lys Leu Glu Ile Lys Arg
                100                 105
```

```
<210> SEQ ID NO 5
<211> LENGTH: 5
<212> TYPE: PRT
<213> ORGANISM: Homo sapien

<400> SEQUENCE: 5

Ile Tyr Gly Ala His
  1               5
```

```
<210> SEQ ID NO 6
<211> LENGTH: 16
<212> TYPE: PRT
<213> ORGANISM: Homo sapien

<400> SEQUENCE: 6

Val Ile Trp Ala Gly Gly Ser Thr Asn Tyr Asn Ser Ala Leu Met Ser
 1               5                  10                  15

<210> SEQ ID NO 7
<211> LENGTH: 12
<212> TYPE: PRT
<213> ORGANISM: Homo sapien

<400> SEQUENCE: 7

Asp Gly Ser Ser Pro Tyr Tyr Tyr Ser Met Glu Tyr
 1               5                  10

<210> SEQ ID NO 8
<211> LENGTH: 10
<212> TYPE: PRT
<213> ORGANISM: Homo sapien

<400> SEQUENCE: 8

Ser Ala Thr Ser Ser Val Ser Tyr Met His
 1               5                  10

<210> SEQ ID NO 9
<211> LENGTH: 7
<212> TYPE: PRT
<213> ORGANISM: Homo sapien

<400> SEQUENCE: 9

Ser Thr Ser Asn Leu Ala Ser
 1               5

<210> SEQ ID NO 10
<211> LENGTH: 9
<212> TYPE: PRT
<213> ORGANISM: Homo sapien

<400> SEQUENCE: 10

Gln Gln Arg Ser Ser Tyr Pro Phe Thr
 1               5

<210> SEQ ID NO 11
<211> LENGTH: 19
<212> TYPE: DNA
<213> ORGANISM: Homo sapien

<400> SEQUENCE: 11
ctgcaggaag aaatcggca                                               19

<210> SEQ ID NO 12
<211> LENGTH: 19
<212> TYPE: DNA
<213> ORGANISM: Homo sapien

<400> SEQUENCE: 12
atgctcggtg tggagaagc                                               19

<210> SEQ ID NO 13
<211> LENGTH: 19
<212> TYPE: DNA
<213> ORGANISM: Homo sapien
```

-continued

```
<400> SEQUENCE: 13
ctgcaggaag aaatcggca                                                    19

<210> SEQ ID NO 14
<211> LENGTH: 21
<212> TYPE: DNA
<213> ORGANISM: Homo sapien

<400> SEQUENCE: 14
tgtgattcct caaacaggcc t                                                 21
```

METHODS OF USE OF SIALOADHESIN FACTOR-2 ANTIBODIES

CROSS-REFERENCE TO RELATED APPLICATIONS

This is a divisional of Ser. No. 10/232,187 filed Aug. 29, 2002 now abandoned which is a continuation-in-part of application of PCT International Application No. PCT/US01/07193, filed Mar. 5, 2001, now pending, which claims benefit of U.S. Provisional Application No. 60/187,595, filed Mar. 7, 2000. This continuation-in-part application also claims the benefit of U.S. Provisional Application Nos. 60/315,943, filed Aug. 30, 2001,60/349,830, filed Jan. 18, 2002, and 60/394,741, filed Jul. 10, 2002.

STATEMENT REGARDING FEDERALLY SPONSORED RESEARCH OR DEVELOPMENT

This invention resulted from research funded in whole or in part by the National Institutes of Health, Grant No. AI41472. The Federal Government has certain rights in this invention.

FIELD OF THE INVENTION

This invention relates to monoclonal antibodies (mAbs) that bind to sialoadhesin factor-2 (SAF-2) and to the use of such antibodies for diagnostic and therapeutic purposes. This invention also relates to the prevention and treatment of diseases and conditions mediated by cells expressing SAF-2.

BACKGROUND OF THE INVENTION

Eosinophils, basophils and mast cells have been implicated as the major cell types producing inflammatory mediators in response to helminthic infections, as well as several diseases, particularly asthma, rhinitis, and atopic dermatitis (Weller, P. F. (1991) *N. Engl. J. Med.* 324:1110; Sur, S., C. et al. (1993) In *Allergy Principles and Practice*. E. Middleton et al. eds. Mosby, St. Louis, Mo., p. 169; Costa, J. J. et al. (1997) *JAMA* 278:1815). In these situations, the preferential accumulation and activation of these cells has been noted. Although considerable progress has been made in our understanding of eosinophil recruitment to the site of inflammation, a number of key points are still unclear, including the exact mediators utilized for localization to these sites during the migration process. For example, activation of microvascular endothelial cells and expression of adhesion molecules, notably VCAM-1, is felt to be a key event in this process during allergic inflammation (Bochner, B. S. (1998) In *Allergy Principles and Practice*. J. Middleton et al. eds. Mosby, St. Louis). In addition, a number of chemokines and other chemotactic factors, such as those acting via CCR3, have been implicated because of their involvement in eosinophil, basophil and mast cell chemotaxis (Dahinden, C. A. et al. (1994) *J. Exp. Med.* 179:751; Daffern, P. J. et al. (1995) *J. Exp. Med.* 181:2119; Nickel, R., L. et al. (1999) *J. Allergy Clin. Immunol.* 104:723; Romagnani, P. et al. (1999) *Am. J. Pathol* 155:1195; Rot, A. et al. (1992) *J. Exp. Med.* 176:1489). Another possibility, however, is that these cells are selectively recruited and activated in a specific way due to a unique cell surface phenotype. While eosinophils, basophils and mast cells are readily identifiable based on their tinctorial properties, as yet there has been no cell surface marker identified that is unique to these cell subsets (Saito, H. et al. (1986) *Blood* 67:50; Bodger, M. P. et al. (1987) *Blood* 69:1414).

Sialoadhesin factor-2, or SAF-2 (European Patent Publication No. EP 0 924 297 A1), is a member of the sialoadhesin family of proteins also known as the 1-type lectins and recently renamed the siglec family (sialic acid-binding Ig-like lectins) (Kelm, S. et al. (1996) *Glycoconjugate Journal* 13:913). The family members include sialoadhesin (siglec-1), CD22 (siglec-2), CD33 (siglec-3), myelin associated glycoprotein (MAG or siglec-4), siglec-5 (Cornish, A. L. et al. (1998) *Blood* 92:2123), OB-BP-1/siglec-6 (Patel, N. et al. (1999) *J. Biol. Chem.* 274:22729) and AIRM1 or siglec-7 (Falco, M. et al. (1999) *J. Exp. Med.* 190:793; Nicoll, G. et al. (1999) *J. Biol. Chem.* 274:34089). With the exception of siglec-4, all are expressed on various subsets of hematopoietic cells. Siglecs belong to the immunoglobulin (Ig) supergene family and have an N-terminal V-set Ig domain followed by 1-16 C2 set Ig domains. Siglecs mediate sialic acid-dependent adhesion with other cells generally preferring either $\alpha 2,3$ linkages (siglec-1, -3, and -4) or $\alpha 2,6$ linkages (siglec-2) (Kelm et al. supra). Most family members have either immunoreceptor tyrosine-based inhibition motifs (ITIM) or activation motifs (ITAM) that participate in signaling through Src homology 2 (SH2) domain binding to the phosphotyrosine of the ITIM or ITAM. This has been demonstrated for CD22, CD33 and AIRM1 (Falco et al., supra; Freeman, S. D. et al. (1995) *Blood* 85:2005; Blasioli, J. et al. (1999) *J. Biol. Chem.* 274:2302).

SAF-2, now known as Siglec-8, exists in two isoforms with identical extracellular and transmembrane sequences. One isoform has a short cytoplasmic tail with no known signaling sequences (Siglec-8), while the other, Siglec-8 long form (Siglec-8L), has a longer cytoplasmic tail containing two tyrosine-based signaling motifs (Foussias, G. et al. (2000) *Biochem Biophys Res Commun* 278:775; Munday, J. et al. (2001) *Biochem. J.* 355:489). Although the function of Siglec-8 and Siglec-8L, and indeed most Siglecs, is unknown, the cytoplasmic region of Siglec-8L contains one consensus immunoreceptor tyrosine-based inhibitory motif (ITIM) and a signaling lymphocyte activation molecule (SLAM)-like motif, suggesting that Siglec-8L may possess signal transduction activity.

SUMMARY OF THE INVENTION

One aspect of the present invention includes an antibody that binds to human SAF-2. More specifically, the present invention includes a monoclonal antibody having the identifying characteristics of monoclonal antibody 2C4. A specific embodiment of this aspect of the present invention is an antibody comprising a heavy chain variable region polypeptide as set forth in SEQ ID NO:2 and a kappa light chain variable region polypeptide as set forth in SEQ ID NO:4.

The present invention also includes an immunoglobulin heavy chain complementarity determining region comprising any of the polypeptides set forth in SEQ ID NOs:5, 6 or 7 or any combination thereof, and an immunoglobulin kappa light chain complementarity determining region comprising any of the polypeptides set forth in SEQ ID NOs:8, 9 or 10 or any combination thereof. A preferred embodiment of the present invention is a polypeptide comprising an immunoglobulin complementarity determining region comprising the polypeptides set forth in SEQ ID NOs:5, 6, 7, 8, 9 and 10. The present invention also includes an isolated polynucleotide encoding any of the forgoing polypeptides.

An additional embodiment of the present invention is a method for detecting the presence of a cell in a sample wherein the cell comprises an SAF-2 protein, the method comprising a) exposing the sample to an antibody that binds to SAF-2 and b) detecting the antibody that is bound to SAF-2. The sample suspected of containing the cell can optionally be treated before exposure to the antibody in order to render the SAF-2 susceptible to binding by the antibody. The preferred utility for this embodiment is the detection of eosinophils.

Another aspect of the instant invention is a method for the prevention and treatment of a disease and condition mediated by cells expressing SAF-2, the method comprising administering to a subject in need thereof an effective amount of a pharmaceutical composition that comprises a therapeutic agent that binds to SAF-2. Preferred is a method for treating or preventing an allergic, asthmatic or cancerous disease state, as well as hypereosinophilic syndromes. Most preferred is a method for preventing or treating asthma, allergic rhinitis, nasal polyposis, atopic dermatitis, chronic urticaria, mastocytosis or eosinophilic or basophilic leukemias. A preferred therapeutic agent that comprises the composition for use in the method is a monoclonal antibody or fragment thereof which binds to human SAF-2 and has the identifying characteristics of monoclonal antibody 2C4.

Yet another aspect of the present invention includes a pharmaceutical composition comprising an effective amount of a therapeutic agent that binds to SAF-2. A preferred therapeutic agent is a monoclonal antibody against human SAF-2 having the identifying characteristics of monoclonal antibody 2C4.

BRIEF DESCRIPTION OF THE DRAWINGS

FIG. 1 shows the $V_H$ cDNA sequence and the deduced amino acid sequence of a monoclonal antibody that binds to SAF-2, mAb 2C4 (SEQ ID NOs:1 and 2, respectively). The bolded residues indicate the three CDRs (SEQ ID NOs:5, 6, and 7).

FIG. 2 shows the $v_K$ cDNA sequence and the deduced amino acid sequence of a monoclonal antibody that binds to SAF-2, 2C4 (SEQ ID NOs:3 and 4, respectively). The bolded residues indicate the three CDRs (SEQ ID NOs:8, 9, and 10).

FIG. 5 demonstrates that Siglec-8 ligation induces eosinophil apoptosis. Eosinophils were cultured as indicated, harvested and analyzed by flow cytometry for annexin-V labeling. Data are from six experiments.

FIG. 6 demonstrates the effect of IL-5 and GM-CSF on Siglec-8 crosslinking-induced eosinophil death. In panel a, IL-5 (1 ng/ml) was added simultaneously at the beginning of the cell culture and viability determined at various time points as indicated. Data are from 4-6 experiments. In panel b, IL-5 or GM-CSF (each used at 30 ng/ml) reduces the concentration of Siglec-8 mAb needed to induce maximal eosinophil apoptosis. Eosinophils were initially cultured with IL-5 or GM-CSF in the presence of secondary Ab and the indicated concentrations of 2E2. After 24 h, apoptosis was analyzed using annexin-V staining. Data are presented as mean±SD, n=2.

DETAILED DESCRIPTION OF THE INVENTION

Figure 3:
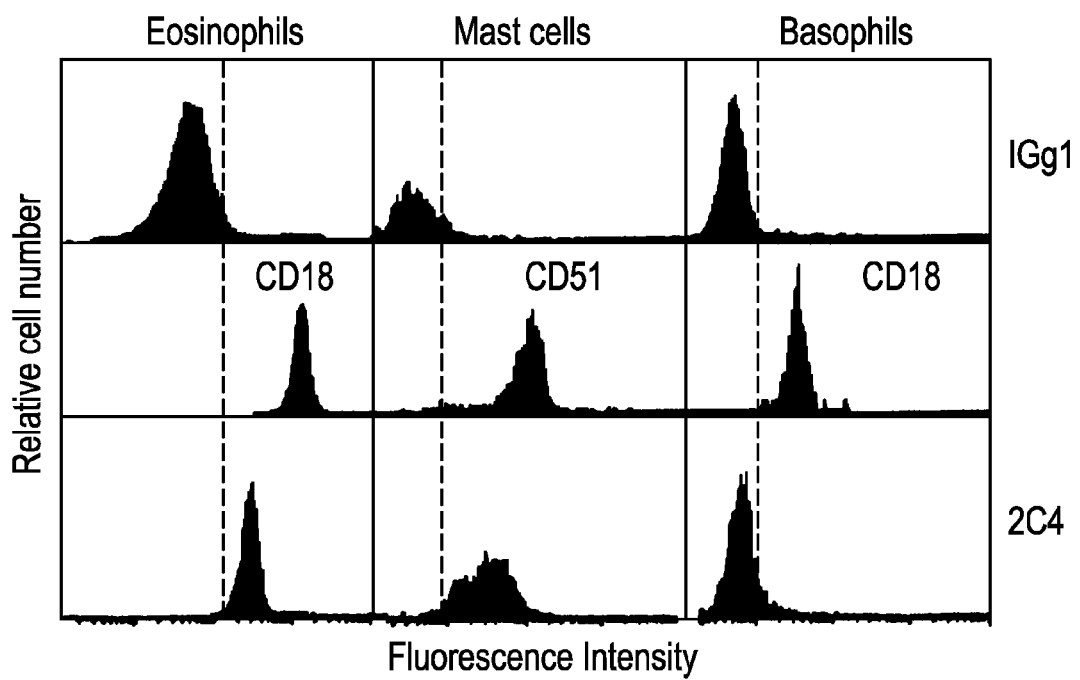
FIG. 3 presents data on expression of SAF-2 on human peripheral blood eosinophils, basophils and 16 week old cord blood-derived cultured mast cells. Histograms shown are representative of 3-4 experiments with virtually identical results for each cell type. Monoclonal reagents used as positive and negative controls are also shown.

The present invention provides a variety of antibodies, including altered antibodies and fragments thereof, directed against SAF-2, which are characterized by their ability to bind to human SAF-2 polypeptide or polypeptides derived therefrom. Exemplary of this class of antibodies is monoclonal antibody 2C4. These antibody products are useful in the detection of cells comprising SAF-2 polypeptide including the specific detection of eosinophils. These antibody products are also useful in therapeutic and pharmaceutical compositions for treating allergic rhinitis, allergies, asthma, eczema, or diseases such as lymphoma, leukemia, or systemic mastocytosis. Alternatively, the antibodies of the invention can be coupled to toxins, antiproliferative drugs or radionuclides to kill cells in areas of excessive SAF-2 expression, thereby treating allergic rhinitis, allergies, asthma, eczema, or diseases such as lymphoma, leukemia, or systemic mastocytosis.

The instant invention also provides a novel means to treat or prevent various disease states that are mediated by cells (or molecules by such cells) expressing SAF-2. These disease states include various allergies, asthma and cancers. The instant invention pertains to the findings that SAF-2 represents a unique cell surface marker for a circumscribed set of cells (eosinophils, basophils and mast cells), and that binding of therapeutic agent, such as an antibody or an altered antibody (as defined herein), results in the specific reduction in such cells that mediate such disease states.

"Therapeutic agent" refers to a prophylactically or therapeutically effective molecule, including a polypeptide, an antibody or altered antibody, and an agonist/antagonist peptide or small molecule compound.

"Antibodies" refers to immunoglobulins which can be prepared by conventional hybridoma techniques, phage display combinatorial libraries, immunoglobulin chain shuffling and humanization techniques. Also included are fully human monoclonal antibodies. As used herein, "antibody" also includes "altered antibody" which refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, Fab' or F(ab')$_2$ and the like. The terms Fv, Fc, Fd, Fab, Fab' or F(ab')$_2$ are used with their standard meanings. See, e.g., Harlow et al. in "Antibodies A Laboratory Manual", Cold Spring Harbor Laboratory, (1988).

"CDRs" are defined as the complementarity determining region amino acid sequences of an antibody which are the hypervariable regions of immunoglobulin heavy and light chains. See, e.g., Kabat et al., *Sequences of Proteins of Immunological Interest,* 4th Ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs share or retain the same antigen binding specificity and/or antagonist ability as the donor antibody from which they were derived, yet may exhibit increased affinity for the antigen. An exemplary process for obtaining analogs is affinity maturation by means of phage display technology as reviewed by Hoogenboom (1997) *Trends in Biotechnology* 15:62; Barbas et al. (1996) *Trends in Biotechnology* 14:230; and Winter et al. (1994) *Ann. Rev. Immunol.* 12:433 and described by Irving et al. (1996) *Immunotechnology* 2:127.

"Altered immunoglobulin coding region" refers to a nucleic acid sequence encoding an altered antibody of the invention. When the altered antibody is a complementarity determining region-grafted (CDR-grafted) or humanized antibody, the sequences that encode the CDRs from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. in "Sequences of Proteins of Immunological Interest", 4th Ed., U.S. Department of Health and Human Services, National Institutes of Health (1987) disclose rules for locating CDRs. In addition, computer programs are known which are useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably, it is an immunoglobulin gene. The second immunoglobulin partner may include a nucleic acid sequence encoding the entire constant region for the same (i.e., homologous, where the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or $F(ab')_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

The term "donor antibody" refers to a monoclonal or recombinant antibody which contributes the nucleic acid sequences of its variable regions, CDRs or other functional fragments or analogs thereof to a first immunoglobulin partner, so as to provide the altered immunoglobulin coding region and resulting expressed altered antibody with the antigenic specificity and neutralizing activity characteristic of the donor antibody. Donor antibodies suitable for use in this invention is a murine monoclonal antibody designated as 2C4.

The term "acceptor antibody" refers to monoclonal or recombinant antibodies heterologous to the donor antibody, which contributes all, or a portion, of the nucleic acid sequences encoding its heavy and/or light chain framework regions and/or its heavy and/or light chain constant regions or V region subfamily consensus sequences to the first immunoglobulin partner. Preferably, a human antibody is the acceptor antibody.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulins. In addition, framework support residues may be altered to preserve binding affinity. See, e.g., Queen et al. (1089) *Proc. Natl Acad Sci USA* 86:10029; Hodgson et al. (1991) *Bio/Technology* 9:421). Furthermore, as described herein, additional residues may be altered to preserve the activity of the donor antibody.

By "sharing the antigen binding specificity" is meant, for example, that although mAb 2C4 may be characterized by a certain level of binding activity, a polypeptide encoding a CDR derived from mAb 2C4 in any appropriate structural environment may have a lower or higher activity. It is expected that CDRs of mAb 2C4 in such environments will nevertheless recognize the same epitope(s) as mAb 2C4.

The phrase "having the identifying characteristics of" as used herein indicates that such antibodies or polypeptides share the same antigen binding specificity as the antibodies exemplified herein, and bind to the specific antigen with a substantially similar affinity as the antibodies exemplified herein as measured by methods well known to those skilled in this art.

A "functional fragment" is a partial heavy or light chain variable sequence (e.g., minor deletions at the amino or carboxy terminus of the immunoglobulin variable region) which shares the same antigen binding specificity as the antibody from which the fragment was derived.

An "analog" is an amino acid sequence modified by at least one amino acid, wherein said modification can be chemical or a substitution or a rearrangement of a few amino acids (i.e., no more than 10) and corresponding nucleic acid sequences, which modification permits the amino acid sequence to retain the biological characteristics, e.g., antigen specificity and high affinity, of the unmodified sequence. Exemplary nucleic acid analogs include silent mutations which can be constructed, via substitutions, to create certain endonuclease restriction sites within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore (Pharmacia) system, or other non-protein substances useful in the medical field and safe for administration to humans and animals. Other effector agents may include a macrocycle, for chelating a heavy metal atom or radioisotopes. Such effector agents may also be useful to increase the half-life of the altered antibodies, e.g., polyethylene glycol.

As used herein, the term "treating" and derivatives thereof means prophylactic, palliative or therapeutic therapy.

For use in constructing the antibodies, altered antibodies and fragments of this invention, a non-human species such as bovine, ovine, monkey, chicken, rodent (e.g., murine and rat) may be employed to generate a desirable immunoglobulin upon presentment with human SAF-2 or a peptide epitope therefrom. Conventional hybridoma techniques are employed to provide a hybridoma cell line secreting a non-human mAb to SAF-2. Such hybridomas are then screened for binding activity as described in the Examples section. Alternatively, fully human mAbs can be generated by techniques known to those skilled in the art.

An exemplary mAb of the present invention is mAb 2C4, a murine antibody which can be used for the development of a chimeric or humanized molecule. The 2C4 mAb is characterized by specific binding activity on human SAF-2. This mAb is produced by the hybridoma cell line 2C4.

The present invention also includes the use of Fab fragments or F(ab')$_2$ fragments derived from mAbs directed against SAF-2 as bivalent fragments. These fragments are useful as agents having binding activity to SAF-2. A Fab fragment contains the entire light chain and amino terminal portion of the heavy chain. An F(ab')$_2$ fragment is the fragment formed by two Fab fragments bound by disulfide bonds. The mAb 2C4 and other similar high affinity antibodies provide sources of Fab fragments and F(ab')$_2$ fragments which can be obtained by conventional means, e.g., cleavage of the mAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

The Fab and F(ab')$_2$ fragments can be constructed via a combinatorial phage library (see, e.g., Winter et al. (1994) *Ann. Rev. Immunol.* 12:433) or via immunoglobulin chain shuffling (see, e.g., Marks et al. (1992) *Bio/Technology* 10:779), wherein the Fd or $V_H$ immunoglobulin from a selected antibody (e.g., 2C4) is allowed to associate with a repertoire of light chain immunoglobulins, $V_L$ (or $V_K$), to form novel Fabs. Conversely, the light chain immunoglobulin from a selected antibody may be allowed to associate with a repertoire of heavy chain immunoglobulins, $V_H$ (or Fd), to form novel Fabs. Anti-SAF-2 mAbs can be obtained by allowing the Fd of mAb 2C4 to associate with a repertoire of light chain immunoglobulins. Hence, one is able to recover Fabs with unique sequences (nucleotide and amino acid) from the chain shuffling technique.

The mAb 2C4 may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions can be used to create restriction enzyme sites which facilitate insertion of mutagenized CDR and/or framework regions. These CDR-encoding regions can be used in the construction of the humanized antibodies of the invention.

The nucleic and amino acid sequences of the heavy chain variable region of mAb 2C4 is set forth in SEQ ID NO:1. The CDR amino acid sequences from this region are set forth in SEQ ID NOs: 5, 6 and 7.

The nucleic and amino acid sequences of the light chain variable region of mAb 2C4 set forth in SEQ ID NO:3. The CDR amino acid sequences from this region are set forth in SEQ ID NOs: 8, 9 and 10.

Taking into account the degeneracy of the genetic code, various coding sequences may be constructed which encode the variable heavy and light chain amino acid sequences and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions to the DNA sequences. See, T. Maniatis et al., *Molecular Cloning: A Laboratory Manual*, Cold Spring Harbor Laboratory (1982), pp. 387-389. An example of one such stringent hybridization condition is hybridization at 4×SSC at 65° C., followed by a washing in 0.1×SSC at 65° C. for one hour. Alternatively, an exemplary stringent hybridization condition is 50% formamide, 4×SSC at 42° C. Preferably, these hybridizing DNA sequences are at least about 18 nucleotides in length, i.e., about the size of a CDR.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an anti-SAF-2 antibody, preferably a high-affinity antibody such as provided by the present invention, inserted into a first immunoglobulin partner such as a human framework or human immunoglobulin variable region.

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of human SAF-2 may be designed to elicit enhanced binding with the same antibody.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent, may be by any suitable means, e.g., by conventional covalent or ionic bonds, protein fusions, or hetero-bifunctional cross-linkers, e.g., carbodiimide, glutaraldehyde and the like. Such techniques are known in the art and are described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified by techniques known to those skilled in the art to enhance expression and intra- and intercellular trafficking.

A preferred altered antibody contains a variable heavy and/or light chain peptide or protein sequence having the antigen specificity of mAb 2C4, e.g., the $V_H$ and $V_L$ chains. Still another desirable altered antibody of this invention is characterized by the amino acid sequence containing at least one, and preferably all of the CDRs of the variable region of the heavy and/or light chains of the murine antibody molecule 2C4 with the remaining sequences being derived from a human source, or a functional fragment or analog thereof.

In a further embodiment, the altered antibody of the invention may have attached to it an additional agent. For example, recombinant DNA technology may be used to produce an altered antibody of the invention in which the Fc fragment or CH2 CH3 domain of a complete antibody molecule has been replaced by an enzyme or other detectable molecule, i.e., a polypeptide effector or reporter molecule. Other additional agents include toxins, antiproliferative drugs and radionuclides.

The second immunoglobulin partner may also be operatively linked to a non-immunoglobulin peptide, protein or fragment thereof heterologous to the CDR-containing sequence having antigen specificity to human SAF-2. The resulting protein may exhibit both antigen specificity and characteristics of the non-immunoglobulin upon expression. That fusion partner characteristic may be, for example, a functional characteristic such as another binding or receptor domain or a therapeutic characteristic if the fusion partner is itself a therapeutic protein or additional antigenic characteristics.

Another desirable protein of this invention may comprise a complete antibody molecule, having full length heavy and light chains or any discrete fragment thereof, such as the Fab or F(ab')$_2$ fragments, a heavy chain dimer or any minimal recombinant fragments thereof such as an Fv or a single-chain antibody (SCA) or any other molecule with the same specificity as the selected donor monoclonal antibody, e.g., mAb 2C4. Such protein may be used in the form of an altered antibody or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin constant regions and variable framework regions from one source, e.g., the acceptor antibody, and one or more (preferably all) CDRs from the donor antibody, e.g., mAb 2C4. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of an anti-SAF-2 mAb (optionally modified as described) or one or more of the heavy or light chain CDRs. The engineered antibodies of the invention exhibit binding activity.

Such engineered antibodies may include a humanized antibody containing the framework regions of a selected human immunoglobulin or subtype or a chimeric antibody containing the human heavy and light chain constant regions fused to the anti-SAF-2 mAb functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the V region frameworks of the donor antibody or V region subfamily consensus sequences (on an amino acid basis) may be suitable to provide a heavy chain variable framework region for insertion of the donor CDRs. A suitable acceptor antibody capable of donating light chain variable framework regions may be selected in a similar manner. It should be noted that the acceptor antibody heavy and light chains are not required to originate from the same acceptor antibody.

Preferably, the heterologous framework and constant regions are selected from human immunoglobulin classes and isotypes, such as IgG (subtypes 1 through 4), IgM, IgA, and IgE. IgG1, k and IgG4, k are preferred. Particularly preferred is IgG 4, k. Most particularly preferred is the IgG4 subtype variant containing the mutations S228P and L235E (PE mutation) in the heavy chain constant region which results in reduced effector function. This IgG4 subtype variant is known herein as IgG4PE. See U.S. Pat. Nos. 5,624,821 and 5,648,260.

The acceptor antibody need not comprise only human immunoglobulin protein sequences. For instance, a gene may be constructed in which a DNA sequence encoding part of a human immunoglobulin chain is fused to a DNA sequence encoding a non-immunoglobulin amino acid sequence such as a polypeptide effector or reporter molecule.

A particularly preferred humanized antibody contains CDRs of mAb 2C4 inserted into the framework regions of a selected human antibody sequence. For humanized antibodies, one, two or preferably three CDRs from mAb 2C4 heavy chain and/or light chain variable regions are inserted into the framework regions of the selected human antibody sequence, replacing the native CDRs of the human antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use such as the treatment of allergic rhinitis, allergies, asthma, eczema, or diseases such as lymphoma, leukemia, or systemic mastocytosis.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both. These substitutions could be supplied by the donor antibody or consensus sequences from a particular subgroup.

In addition, the constant region may be altered to enhance or decrease selective properties of the molecules of this invention. For example, dimerization, binding to Fc receptors, or the ability to bind and activate complement (see, e.g., Angal et al. (1993) *Mol. Immunol.* 30:105; Xu et al. (1994) *J. Biol. Chem.* 269: 3469; European Patent Publication No. EP 0 307 434 B1).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may be useful for treating allergic rhinitis, allergies, asthma, eczema, or diseases such as lymphoma, leukemia, or systemic mastocytosis.

Preferably, the variable light and/or heavy chain sequences and the CDRs of mAb 2C4 or other suitable donor mAbs and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the murine antibody 2C4, is conventionally cloned and the DNA of its heavy and light chain variable regions obtained by techniques known to one of skill in the art, e.g., the techniques described in Sambrook et al., *Molecular Cloning: A Laboratory Manual*, 2nd edition, Cold Spring Harbor Laboratory (1989). The variable heavy and light regions containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin, are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody are identified using computerized databases, e.g., KABAT®, and a human antibody characterized by homology to the V region frameworks of the donor antibody or V region subfamily consensus sequences (on an amino acid basis) to mAb 2C4 is selected as the acceptor antibody. The sequences of synthetic heavy chain variable regions containing the CDR-encoding regions within the human antibody frameworks are designed with optional nucleotide replacements in the framework regions to incorporate restriction sites. This designed sequence is then synthesized using long synthetic oligomers. Alternatively, the designed sequence can be synthesized by overlapping oligonucleotides, amplified by polymerase chain reaction (PCR), and corrected for errors. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention may be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells.

A conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV or Rous Sarcoma virus promoter, and signal sequences, which can be derived from other known antibodies. Similarly, a second expression vector can be produced having a DNA sequence which encodes a complementary antibody light or heavy chain. Preferably, this second expression vector is identical to the first except with respect to the coding sequences and selectable markers, in order to ensure, as much as possible, that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by an appropriate assay such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the pUC series of cloning vectors, such as pUC19, which is commercially available from vendors such as Amersham or Pharmacia, may be used. Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV or Rous Sarcoma virus promoters) which direct the replication and expression of heterologous DNA sequences in selected host cells. These vectors contain the above-described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g., replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of E. coli are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3) and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., supra.

Bacterial cells may prove useful as host cells suitable for the expression of the recombinant Fabs of the present invention (see, e.g., Plückthun, A., *Immunol. Rev.*, 130, 151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of E. coli used for expression are well-known as host cells in the field of biotechnology. Various strains of B. subtilis, Streptomyces, other bacilli and the like may also be employed.

Where desired, strains of yeast cells known to those skilled in the art are also available as host cells, as well as insect cells, e.g. Drosophila and Lepidoptera, and viral expression systems. See, e.g. Miller et al., *Genetic Engineering*, 8, 277-298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay.

Following the procedures described for humanized antibodies prepared from mAb 2C4, one of skill in the art may also construct humanized antibodies from other donor antibodies, variable region sequences and CDR peptides described herein. Engineered antibodies can be produced with variable region frameworks potentially recognized as "self" by recipients of the engineered antibody. Modifications to the variable region frameworks can be implemented to effect increases in antigen binding and antagonist activity without appreciable increased immunogenicity for the recipient. Such engineered antibodies may effectively treat a human for ischemic diseases such as myocardial infarction or cerebral stroke or treatment of vascular insufficiency diseases, such as diabetes. Such antibodies may also be useful in the diagnosis of those conditions.

This invention also relates to a method for treating allergic rhinitis, allergies, asthma, eczema, or diseases such as lymphoma, leukemia, or systemic mastocytosis in a mammal, particularly a human, which comprises administering an effective dose of a therapeutic agent that binds to SAF-2. Preferred is an anti-SAF-2 monoclonal antibody. The mAb can include one or more of the antibodies or altered antibodies described herein or fragments thereof. Thus, the therapeutic agents of the present invention, when in preparations and formulations appropriate for therapeutic use, are highly desirable for persons susceptible to or experiencing allergic rhinitis and other allergic diseases, asthma, nasal polyposis, urticaria, hypereosinophilic syndromes (including Churg- Strauss Syndrome and allergic bronchopulmonary Aspergillosis), eczema, or diseases such as lymphoma, leukemia (including eosinophilic and basophilic leukemias) or systemic mastocytosis.

The monoclonal antibodies used in the methods of the invention can include one or more of the antibodies or altered antibodies described herein or fragments thereof. Preferably, the anti-SAF-2 antibody used in the methods of the invention has the identifying characteristics of mAb 2C4.

The altered antibodies, antibodies and fragments thereof of this invention may also be used in conjunction with other antibodies, particularly human mAbs reactive with other markers (epitopes) responsible for the condition against which the engineered antibody of the invention is directed.

The antibodies of the present invention can be formulated into pharmaceutical compositions and administered in the same manner as described for mature proteins. See, e.g., International Patent Application, Publication No. WO90/02762. Generally, these compositions contain a therapeutically effective amount of an antibody of this invention and an acceptable pharmaceutical carrier. Suitable carriers are well known to those of skill in the art and include, for example, saline. Alternatively, such compositions may include conventional delivery systems into which protein of the invention is incorporated. Optionally, these compositions may contain other active ingredients.

The therapeutic agents of this invention may be administered by any appropriate internal route, and may be repeated as needed, e.g., as frequently as one to three times daily for between 1 day to about three weeks to once per week or once biweekly. Preferably, the antibody is administered less frequently than is the ligand, when it is used therapeutically. The dose and duration of treatment relates to the relative duration of the molecules of the present invention in the human circulation, and can be adjusted by one of skill in the art depending upon the condition being treated and the general health of the patient.

As used herein, the term "pharmaceutical" includes veterinary applications of the invention. The term "therapeutically effective amount" refers to that amount of therapeutic agent, which is useful for alleviating a selected condition. These therapeutic compositions of the invention may be administered to mimic the effect of the normal receptor ligand.

This invention provides for a pharmaceutical composition which comprises a therapeutic agent of this invention and a pharmaceutically acceptable carrier, diluent or excipient. Accordingly, the therapeutic agent may be used in the manufacture of a medicament. Pharmaceutical compositions of the therapeutic agent may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, the therapeutic agent may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously or intranasally.

Therapeutic agents of the invention may be prepared as pharmaceutical compositions containing an effective amount of the engineered (e.g., humanized) antibody of the invention as an active ingredient in a pharmaceutically acceptable carrier. In the compositions of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 mL of sterile Ringer's solution, and about 1 mg to about 30 mg and preferably 5 mg to about 25 mg of an engineered antibody of the invention. Actual methods for preparing parenterally administrable compositions are well known or will be apparent to those skilled in the art and are described in more detail in, for example, "Remington's Pharmaceutical Science", 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. Such dose may, if necessary, be repeated at appropriate time intervals selected as appropriate by a physician during the response period.

The present invention may be embodied in other specific forms, without departing from the spirit or essential attributes thereof, and, accordingly, reference should be made to the appended claims, rather than to the foregoing specification or following examples, as indicating the scope of the invention.

All publications including, but not limited to, patents and patent applications, cited in this specification or to which this patent application claims priority, are herein incorporated by reference as if each individual publication were specifically and individually indicated to be incorporated by reference herein as though fully set forth.

EXAMPLES

The present invention will now be described with reference to the following specific, non-limiting examples.

Example 1

Generation of Monoclonal Antibodies

A. Preparation of Recombinant SAF-2

The full length coding region of SAF-2 (see European Patent Publication No. EP 0 924 297 A1, incorporated herein by reference) was subcloned into the mammalian expression vector pCDN (see Aiyar et al. (1994) Mol. Cell. Biochem. 131:75-86) using PCR. The sequence of the insert was confirmed before being transfected into HEK293 cells using $Ca^{++}PO_4$. Clones were selected in 500 µg/mL G418 and evaluated for expression using Northern blot analysis followed by FACS analysis. The extracellular domain of SAF-2 was subcloned by PCR and inserted in frame with a Factor Xa cleavage site and the Fc portion of human IgG1. The sequence was confirmed before the vector was electroporated into CHOEA1 cells. Stably expressing clones were selected, expanded, evaluated for Fc expression and scaled up. The SAF-2/Fc fusion protein was purified from supernate using Protein A Sepharose and an aliquot was cleaved with Factor Xa to generate the SAF-2 polypeptide used for antibody generation.

B. Monoclonal Antibody Generation

Mice were initially immunized with SAF-2 (25 µg) in Freund's complete adjuvant and then received two booster injections (25 µg) 2 and 4 weeks later. On the basis of a good serum antibody titer to SAF-2, one mouse received a further immunization of 20 µg of SAF-2 i.v. in PBS. The spleen was harvested four days later and fused with myeloma cells according to the method described in Zola (Zola, H. (1987) *Monoclonal antibodies: A manual of techniques*. CRC Press, Boca Raton, Fla.).

C. Hybridoma Screening Assay

Positive hybridomas were tested for binding in 96 well microtiter plates coated with SAF-2/Fc at 0.5 µg/mL and detected with europium conjugated anti-mouse IgG.

Specifically, 96-well plates were coated with SAF-2/Fc (100 µL/well in PBS) by incubation overnight at 4° C. The solution was then aspirated and non-specific binding sites were blocked with 250 µL/well of 1% bovine serum albumin (BSA) in TBS buffer (50 mM Tris, 150 mM NaCl, 0.02% Kathon, pH 7.4) for 5-60 minutes at RT. Following this and each of the following steps, the plate was washed 4 times in wash buffer (10 mM Tris, 150 mM NaCl, 0.05% Tween 20, 0.02% Kathon, pH 7.4). To each well, 50 µL hybridoma medium and 50 µl assay buffer (0.5% BSA, 0.05% bovine gamma globulin, 0.01% Tween 40, 20 µM diethylenetriaminepentaacetic acid in TBS buffer) was added and incubated for 60 minutes at RT in a shaker-incubator. To each well was then added 100 µL 0.5 µg/mL Eu3+ labeled anti-mouse antibody in assay buffer. Finally, 200 µL/well of enhancer (Wallac, Tuku, Finland) was added and incubated for 5 minutes at RT, and the time-resolved fluorescence measured. Positives were rescreened by immunoassay and BIAcore and then cloned by the limiting dilution method. Antibodies produced by cloned cell lines were confirmed to be specific for SAF-2 by ELISA, BIAcore and flow cytometry using transfected cell lines.

D. Purification of mAbs

Monoclonal antibodies were purified by ProsepA (Bio Processing, Consett, UK) chromatography, respectively, using the manufacturer's instructions. Monoclonal antibodies were >95% pure by SDS-PAGE.

Example 2

Characterization of Monoclonal Antibodies

A. Isotyping of Monoclonal Antibodies

Monoclonal antibody 2C4 used in this study was isotyped as IgG1 kappa using commercially available reagents (Pharmingen, San Diego, Calif.).

B. Affinity Measurements of Monoclonal Antibodies

The affinity of monoclonal antibody 2C4 was determined using a BIAcore optical biosensor (Pharmacia Biosensor, Uppsala, Sweden) using a flow rate of 30 µL/min. Kinetic data was evaluated using relationships described previously (Karlsson, et al. (1991) *J. Immunol. Meth.* 145:229). The mAb (diluted in HBS buffer, 10 mM HEPES, 150 mM NaCl, 0.01% Tween-20, pH 7.4) was injected over a rabbit anti-mouse IgG Fc surface, followed by buffer flow, and the RU was recorded. SAF-2 (diluted in HBS buffer) was then injected for 180 seconds, followed by a buffer flow for 300 seconds, and the RU was recorded. The sensor chip surface was regenerated by an injection of 0.1M phosphoric acid. The on-rates ($K_a$) and off-rates ($K_d$) of binding were calculated using BIAcore (Uppswala, Sweden) software. The data from this analysis indicated that monoclonal antibody 2C4 displayed an on-rate of ($K_a$) $2.2\times10^5$ $M^{-1}$ $s^{-1}$ and an off-rate of ($K_d$) $4.3\times10^{-5}$ $s^{-1}$, giving a calculated equilibrium constant (KD) of $2.0\times10^{-10}$M.

C. Purification and Culture of Cells

Eosinophils were purified from peripheral blood following Percoll removal of PBMC, lysis of RBC and immunomagnetic negative selection of neutrophils (Hansel, T. T. et al., (1991) *J. Immunol. Methods* 145:105). The resulting population was >95% eosinophils. In some experiments, purified eosinophils were cultured for up to two days in complete RPMI containing 10% FCS and 1 or 10 ng/mL IL-5, or 10 or 50 ng/mL eotaxin (Peprotech, Rocky Hill, N.J.), C3a, or C5a (Advanced Research Technologies) (Matsumoto, K. et al. (1998) *Am. J. Respir. Cell Mol. Biol.* 18:860). Viability after 2 days or less of culture was >80%. Enrichment of peripheral blood for basophils was performed using a double-Percoll density gradient separation, increasing the number of basophils to 3-10% of the total leukocyte count (Bochner, B. S. et al. (1989) *J. Immunol. Methods* 125:265) or with further immunomagnetic negative selection to at least 50%. Human cord blood-derived mast cells were generated as previously reported (Tachimoto, H. et al. (1997) *Int. Arch. Allergy Immunol.* 113:293; Saito, H. et al. (1996) *J. Immunol.* 157:343). The purified CD34+ cells were cultured in IMDM supplemented with 10 μg/mL insulin, 5.5 μg/mL transferrin, 6.7 ng/mL selenium, 5×10-5 M 2-mercaptoethanol, 5% fetal bovine serum, 100 U/mL penicillin, 100 μg/mL streptomycin, 100 ng/mL stem cell factor (generously provided by Amgen, Thousand Oaks, Calif.) and 50 ng/mL IL-6 (Biosource, Camarillo, Calif.) for at least 10 weeks and 1 ng/mL IL-3 (Biosource) for the first 7 days. The purity of mast cells was determined by staining with May-Grünwald and Giemsa reagents, and routinely reached 99-100% by 14-16 weeks of culture. For these experiments, cells used were harvested at 16-17 weeks of culture. Bone marrow derived eosinophils were cultured as follows: light density cells of Ficolled human bone marrow were cultured in IMDM/20% FCS with 20 ng/mL rhGM-CSF and 20 ng/mL rhIL-5 (R&D Systems) at 1.5×106 cells/mL at 37° C., 5% CO2. The cell lines HL-60 and EOL3 were treated with sodium butyrate to differentiate them to a more eosinophil-like phenotype (Collins, S. (1987) *Blood* 70:1233).

D. Expression of SAF-2 on Human Eosinophils, Basophils and Mast Cells

Expression of integrins or SAF-2 was evaluated in anticoagulated whole blood or in enriched cells using single color indirect immunofluorescence and flow cytometry as previously described (Matsumoto, K. et al. (1998) *Am. J. Respir. Cell Mol. Biol.* 18:860; Bochner, B. S. et al. (1989) *J. Immunol. Methods* 125:265). Dual color detection of basophils was also performed (Bochner, B. S. et al. (1989) *J. Immunol. Methods* 125:265). Monoclonal antibodies used included the following: control IgG1, CD18 (7E4), CD51 (AMF7, all Coulter-Immunotech, Hialeah, Fla.), CD9 (Immunotech) and mAb 2C4. Also used was R-phycoerythrin (PE)-conjugated or FITC-conjugated F(ab')2 goat-anti-mouse IgG (Biosource) and FITC-conjugated polyclonal goat anti-human IgE (Kierkegaard and Perry, Gaithersburg, Md.). All samples were fixed in 0.1% paraformaldehyde (Sigma) and analyzed using a FACSCalibur™ flow cytometer (Becton Dickinson, Mountainview, Calif.). At least 1,000 events were collected and displayed on a 4-log scale yielding values for mean fluorescence intensity (MFI).

SAF-2 was localized to eosinophils (FIG. 3) and was absent from other purified cell populations including neutrophils, monocytes, B cells and T cells (data not shown). Activation of purified eosinophils with optimal concentrations of eotaxin, C5a, C3a or IL-5 for 1 hour, 24 or 48 hours before analysis did not alter the levels of SAF-2 expression on the cell surface (data not shown). Two cells lines, HL-60 and EOL3, which have been reported to become more eosinophil-like following differentiation with Na-butyrate for 5 days, were examined for the expression of SAF-2 (Mayumi, M. (1992) *Leukemia & Lymphoma* 7:243). Under these culture conditions, HL-60 and EOL3 failed to express SAF-2 (data not shown). Interestingly, when eosinophils are generated in vitro from bone marrow with IL-5, no SAF-2 expression was noted. Eosinophils could be identified by day 14 by staining with CD9 (3-12% of the cells) and Wright stain (data not shown). It thus appears that SAF-2 expression may be a later marker for eosinophil differentiation.

Low, but consistently detectable levels of SAF-2 were found on basophils (FIG. 3; for mAb 2C4, 21.1±4.0 percent positive; mean±SEM, n=4). Mature human cord blood-derived mast cells also strongly expressed SAF-2, although the pattern of expression was somewhat more heterogeneous than for blood leukocytes in that the peaks were not perfectly unimodal (FIG. 3).

Example 3

Cloning and Sequencing of Heavy and Light Chain Antigen Binding Regions

Full-length $V_H$ and $V_K$ region sequences were obtained for monoclonal antibody 2C4 using the following cloning strategy. The N-terminal amino acid sequences of the mAb 2C4 $V_H$ and $V_K$ were determined. In the event that the N-terminal V region residue was blocked with pyroglutamic acid, enzymatic de-blocking was performed by means of pyroglutamate aminopeptidase.

Total hybridoma RNA was purified, reverse transcribed and PCR amplified. For the heavy chains, the RNA/DNA hybrid was PCR amplified using a mouse IgG CH1-specific primer and a degenerate primer based on the N-terminal protein sequence. Similarly, for the light chains, the RNA/DNA hybrid was PCR amplified using a mouse C kappa primer and a degenerate primer based on the N-terminal protein sequence. PCR products of the appropriate size, i.e., ~350 were cloned into a plasmid vector, and sequenced by a modification of the Sanger method (Sanger et al. (1977) *PNAS USA* 74:5463). In each case, the sequences of multiple $V_H$ clones and the sequences of multiple $V_K$ clones were compared to generate a consensus heavy chain variable region sequence and consensus light chain variable region sequence, respectively. The nucleotide and deduced amino acid sequences of the $V_H$ and $V_K$ regions of monoclonal antibody 2C4 are shown in FIGS. 1 and 2, respectively.

Example 4

Expression of Short (Siglec-8) and Long (Siglec-8L) Forms of SAF-2 on Eosinophils, Basophils and Mast Cells To clarify whether human eosinophils contain Siglec-8 or Siglec-8L, RT-PCR was performed with Siglec-8-specific or Siglec-8L-specific primers on mRNA from eosinophils purified as described previously. Total RNA was prepared with Trizol™ (Life Technologies, Gaithersburg, Md.) according to the manufacturers' instructions. After DNase treatment of total RNA (DNA-Free™, Ambion, Austin, Tex.), cDNAs were synthesized by extension of oligo(dT) primers (Roche Diagnostics, Indianapolis, Ind.) using the GeneAmp™ RNA PCR kit (Perkin Elmer, Foster City, Calif.).

```
Siglec-8 Primers:
5'-CTGCAGGAAGAAATCGGCA-3'      (SEQ ID NO: 11)

5'-ATGCTCGGTGTGGAGAAGC-3'      (SEQ ID NO: 12)

Siglec-8L Primers:
5'-CTGCAGGAAGAAATCGGCA-3'      (SEQ ID NO: 13)

5'-TGTGATTCCTCAAACAGGCCT-3'    (SEQ ID NO: 14)
```

The amplification cycles were 94° C. for 30 seconds, 60° C. for 45 seconds, and 72° C. for 1 minute. After 35 cycles, PCR products were separated by 3% agarose gel electrophoresis and stained with ethidium bromide.

Bands for both Siglec-8 and Siglec-8L were detected from eosinophils. Sequence analysis of these PCR products revealed a 100% match with those in public databases.

Using similar RT-PCR methods, human basophils and HMC-cells also expressed both Siglec-8 and Siglec-8L mRNA.

Example 5

Functional Analysis

Calcium Flux and Chemotaxis

Initial functional assays (Ca++ and chemotaxis) were performed as previously described (Macphee, C. H. et al. (1998) *J. Immunol.* 161:6273). To determine the role of SAF-2 in eosinophil biology, anti-SAF-2 mAbs were analyzed for their ability to affect eosinophil function. First, the antibodies were tested for their ability to cause a Ca++ flux in purified eosinophils either on their own or following crosslinking with a second antibody. Compared with eotaxin, which gave a robust Ca++ response, none of the mAbs to SAF-2 caused a Ca++ flux in eosinophils over a 15 min. time course (data not shown). The mAbs were then tested for the ability to modulate the Ca++ response to eotaxin in purified eosinophils. The eosinophils were preincubated with anti-SAF-2 with or without a crosslinking antibody and then simulated with eotaxin. Again, the mAbs did not influence the Ca++ flux in response to eotaxin. In addition, the mAbs were also evaluated in an eosinophil chemotaxis assay using eotaxin as the chemotactic agent; again the mAbs failed to modulate eosinophil function.

Viability Assays

Viability assays were performed in the presence of monoclonal antibodies described herein. Eosinophils from normal, allergic, and hypereosinophilic donors were purified from peripheral blood as described. Eosinophil purity was consistently >98%, with neutrophils being the only contaminating cells. The viability of freshly isolated eosinophils was >99% as determined by erythrosin-B dye exclusion.

Polyclonal intact and F(ab')$_2$ goat anti-mouse IgG (heavy and light chain) were purchased from Caltag Laboratories (Burlingame, Calif.). Recombinant human IL-5 and GM-CSF were from R&D Systems (Minneapolis, Minn.). Mouse anti-human CD44 mAb (clone J-173, IgG1), anti-Fas/CD95 (clone 7C11, IgM) and anti-CD18 mAb (clone 195N, IgG1) were from Beckman-Coulter (Hialeah, Fla.). Rabbit polyclonal IgG polyhistidine His-1 Ab (mHis6 Ab) was from Santa-Cruz Biotechnology (Santa-Cruz, Calif.). IgG and IgM isotype control Abs were from Sigma-Aldrich (St. Louis, Mo.).

Eosinophils were harvested at different time points over 2-72 h after co-culture with the monoclonal antibodies described herein in the presence or absence of polyclonal goat anti-mouse IgG Ab used for secondary cross-linking. In some experiments, intact versus F(ab')$_2$ goat anti-mouse IgG were compared in order to elucidate any effect of Fc on eosinophil apoptosis. For controls, cells were incubated with medium alone or CD44 mAb in the presence or absence of secondary crosslinking Ab and with or without IL-5 or GM-CSF (1-30 ng/ml). In priming experiments, eosinophils were first preincubated with IL-5 or GM-CSF (30 ng/ml) for 24 h, then various Ab were added for an additional 24 h of culture before analysis of apoptosis.

In certain experiments, viability of cultured eosinophils was determined by erythrosin dye exclusion as assessed by light microscopy (Matsumoto, K., et al. (1995) *Blood* 86:1437; Walsh, G. M., et al. (1998) *J. Immunol. Methods* 217:153). For other experiments, morphological analysis using established light microscopic criteria was performed. Briefly, cytocentrifugation preparations were stained with Leukostat (Fisher Diagnostics, Pittsburgh, Pa.) to reveal nuclear morphology. Apoptotic cells were detected by the condensed and rounded appearance of their nuclei under light microscopy. Cells exhibiting apoptotic nuclei were enumerated in different fields in a blinded manner using a random coded order. At least 500 total cells were counted per slide. Cells were then photographed using a Zeiss Axioscope microscope (Oberkochen, Germany) at 400× magnification. In addition to light microscopic techniques, cell cycle analysis was performed using PI staining (50 mg/ml) of fixed, permeabilized (70% EtOH, 4$_t$C, 30 min), and RNase treated (RNase A, 0.05 mg/ml, 37$_t$C, 30 min) eosinophils. Stained cells were then analyzed by flow cytometry (FACS Calibur, Becton-Dickinson, San Jose, Calif.) as described previously. Finally, annexin-V labeling was used to detect apoptosis in eosinophils (15, 17).

Figure 4:
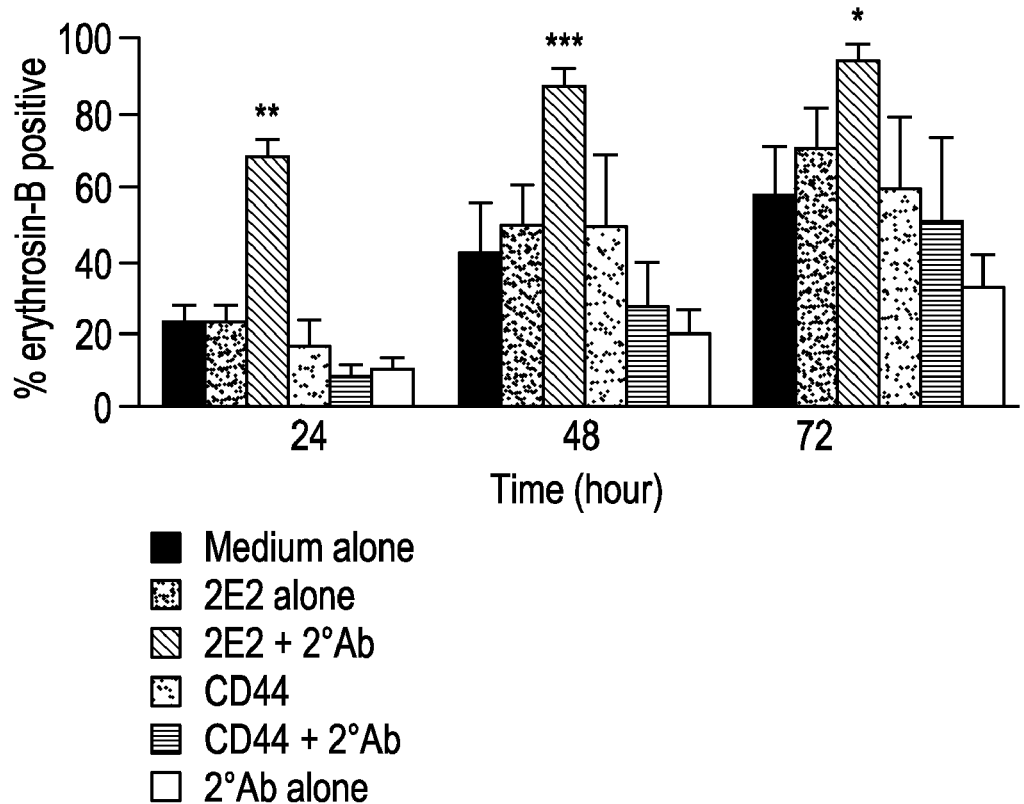
FIG. 4 shows the effect of Siglec-8 crosslinking on eosinophil death. Purified peripheral blood eosinophils were cultured under the indicated conditions. Viability was assessed using erythrosin-B dye exclusion. Data are from six experiments.

Using specific murine monoclonal antibodies against Siglec-8 (note that all subsequent uses of the term Siglec-8 will refer to both isoforms unless specified otherwise) and a secondary polyclonal anti-mouse antibody to enhance crosslinking, we determined whether Siglec-8 ligation inhibited eosinophil survival in vitro. As shown in FIG. 4, Siglec-8 crosslinking with 2E2 mAb plus a secondary polyclonal Ab induced a significant increase in eosinophil death. Determined at 24 h of culture, for example, the percentage of eosinophil death induced by Siglec-8 crosslinking (68±4%), was significantly higher then medium alone (23±4%, p<0.05) or CD44 control crosslinking conditions (9±2%, p<0.0001). The effect of Siglec-8 crosslinking was time dependent, with the levels of eosinophil death increasing to more than 90% by 48-72 h of culture.

Eosinophil death induced by Siglec-8 crosslinking, as assessed by dye exclusion, was already approximately 70% after only 24 h of culture. To further explore the effects of Siglec-8 crosslinking on eosinophil death and to more carefully examine the kinetics, annexin-V staining was used to distinguish apoptosis from necrosis at various time points. FIG. 5 demonstrates a significant increase in annexin-V+ eosinophils as early as 4 h of culture with Siglec-8 crosslinking (15±7%) compared to CD44 control crosslinking (5±3%) or medium control (3±1%), indicating a rapid apoptotic effect (n=6). FIG. 4 also demonstrates that the Siglec-8 effect became even more pronounced by 24-72 h of culture, especially when compared to effects of the survival promoting cytokine, IL-5. For an additional assessment of apoptosis induced by Siglec-8 crosslinking, light microscopic examination of eosinophils was performed. After 24 h of culture, Siglec-8 crosslinking on eosinophils resulted in changes in morphology characterized by reduced cell volume, loss of cytoplasmic content, and condensation of nuclei typical of apoptosis. This was rarely seen in cells cultured with IL-5 or control CD44 crosslinking. As an average from four experiments, the percentage of eosinophils displaying morphological characteristics of apoptosis with Siglec-8 crosslinking was 43±15% compared to 10±2% and 10±1% with medium or CD44 Ab crosslinking, respectively. In parallel experiments, we also studied DNA fragmentation in permeabilized eosinophils, using PI staining in fixed cells. Siglec-8 crosslinking for 24 h increased DNA fragmentation (48% hypodiploid DNA staining), compared to 18% and 21% with medium alone, or CD44 crosslinking, respectively. These data provide multiple lines of evidence demonstrating apoptosis induced by Siglec-8 crosslinking.

Figure 7:
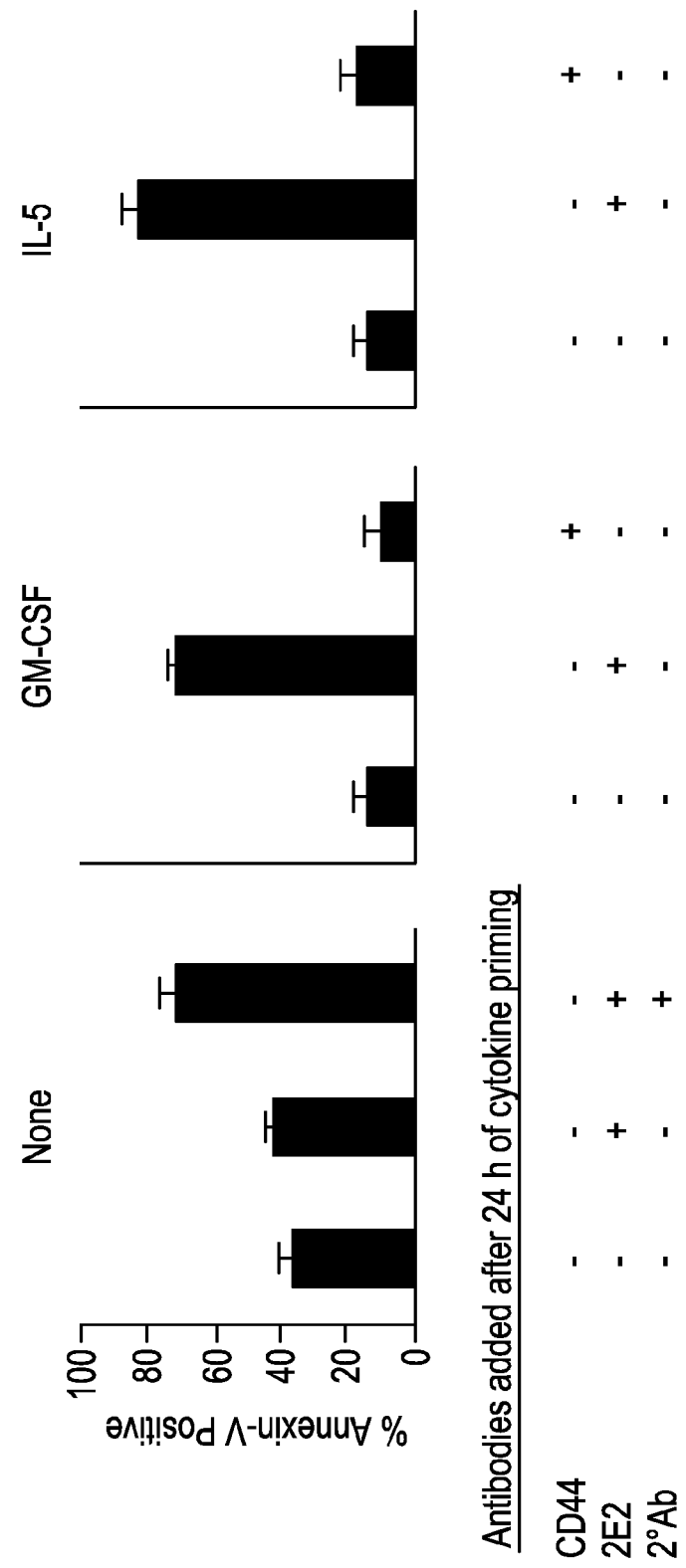
FIG. 7 demonstrates that IL-5 or GM-CSF priming enhances eosinophil apoptosis in response to Siglec-8 mAb. Eosinophils were preincubated with or without IL-5 or GM-CSF (each at 30 ng/ml) for 24 h. Antibodies were then added to the cultures, as indicated, and apoptosis was analyzed using annexin-V staining 24 h later. Data are presented as mean±SD of two experiments.

IL-5 and GM-CSF are potent and specific anti-apoptotic cytokines for eosinophils, and their expression is increased at sites of allergic inflammation in the airways. When eosinophils are cultured in the absence of survival-promoting cytokines, they rapidly undergo apoptosis; in the presence of these cytokines, their survival can be maintained for weeks. Therefore, we examined the effect of IL-5 and GM-CSF on Siglec-8 crosslinking-induced eosinophil apoptosis. When IL-5 (1 ng/ml) was added simultaneously with Siglec-8 crosslinking antibodies at the beginning of the culture, the cytokine could not override the Siglec-8 crosslinking-induced cell death. In fact, at 48 h, the level of eosinophil apoptosis induced by Siglec-8 cross inking in the presence of 1 ng/ml of IL-5 appeared somewhat higher compared to Siglec-8 crosslinking alone (FIG. 6a, n=4). Similar results were obtained using 10 ng/ml of IL-5 or GM-CSF (data not shown). To explore this further, we added higher concentrations of IL-5 or GM-CSF (30 ng/ml) simultaneously with Siglec-8 crosslinking Abs to the initial eosinophil cultures. Both IL-5 and GM-CSF significantly enhanced Siglec-8-induced apoptosis. The percentage of apoptosis increased from 53±5% to 74±3% and 76±3% with IL-5 or GM-CSF, respectively (n=4). To determine whether these cytokines were enhancing eosinophil sensitivity to undergo apoptosis induced by Siglec-8 ligation, experiments were performed in which cells were cultured with saturating to subsaturating concentrations of Siglec-8 mAb in the presence or absence of IL-5, GM-CSF (30 ng/ml) or secondary Ab. Addition of IL-5 or GM-CSF markedly enhanced eosinophil apoptosis even when sub-saturating concentrations of Siglec-8 mAb (0.25 mg/ml) were used (FIG. 6b). These data suggest that the presence of IL-5 or GM-CSF rendered eosinophils more sensitive to Siglec-8 crosslinking effects with respect to its apoptotic effect. Therefore, one additional set of experiments was performed to determine whether eosinophil priming with these cytokines, prior to addition of Siglec-8 crosslinking antibodies, enhanced the pro-apoptotic effect. Eosinophils were preincubated with IL-5 or GM-CSF for 24 h, then mAbs were added and cells were cultured for an additional 24 h, after which apoptosis was analyzed. Remarkably, cytokine priming (4-30 ng/ml) led to a profound pro-apoptotic response in the presence of Siglec-8 mAb alone (FIG. 7 and data not shown), a response not seen in the absence of cytokines. Note that the percentage of apoptosis in the presence of IL-5 alone or CD44 control Ab alone was 14±3%, and 15±5%, respectively (FIG. 7, n=2). Levels of apoptosis with 2E2 mAb alone (69±4%) in IL-5-primed eosinophils were similar to those seen in unprimed eosinophils exposed to both 2E2 and secondary Ab (72±5%). Similar results were obtained using GM-CSF (FIG. 7).

Figure 8:
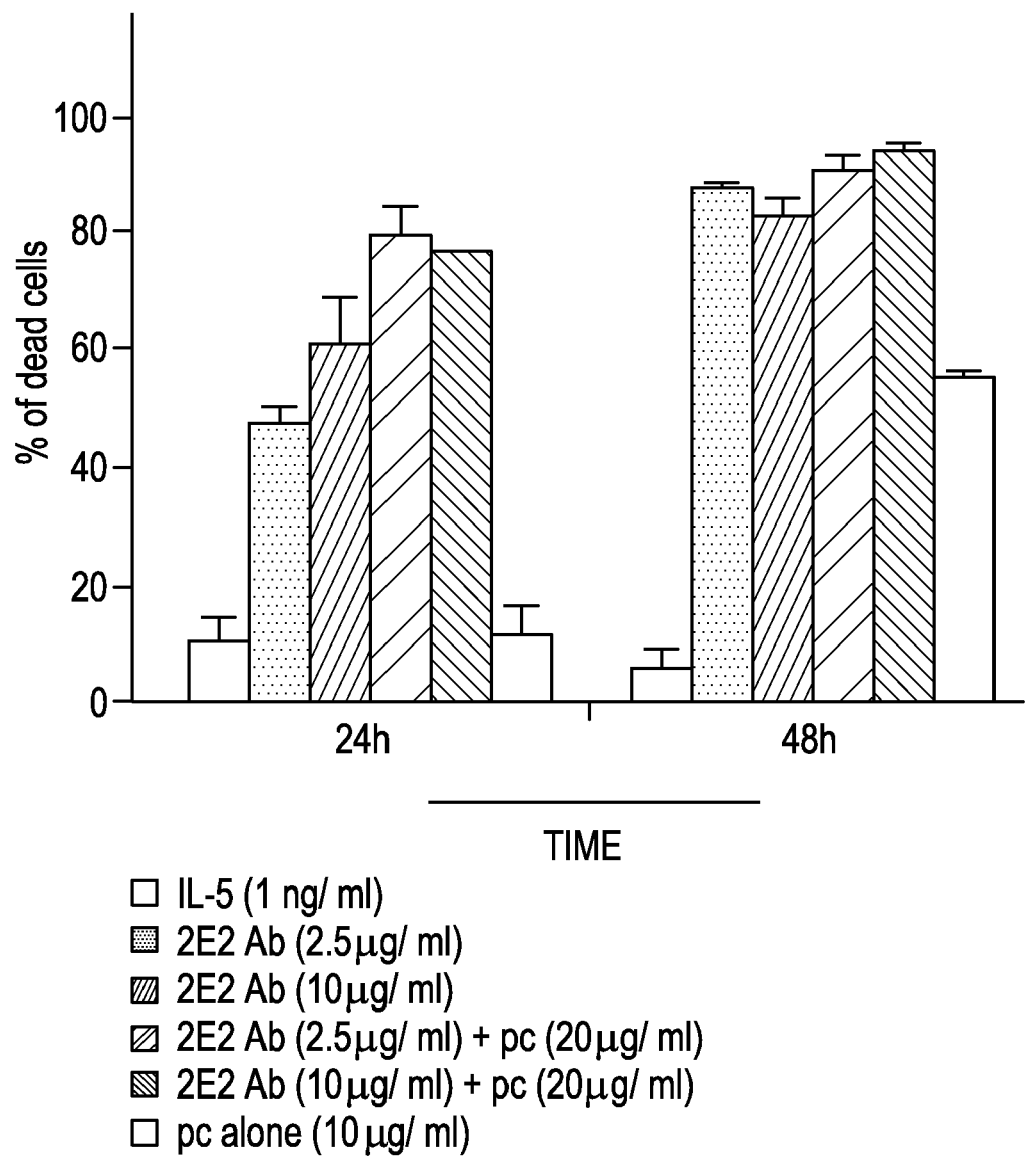
FIG. 8 demonstrates that monoclonal antibodies to Siglec-8 either alone or in the presence of a secondary, crosslinking antibody (pc) induces cellular death in eosinophils obtained from bronchoalveolar lavage fluid after segmental allergen challenge. Siglec-8 antibody (2E2 Ab) was used at two different concentrations: 2.5 and 10 ug/ml (n=1, data presented as mean+/−SEM of a duplicate set of experiments).

Crosslinking of Siglec-8 on eosinophils isolated after allergen challenge of the lower airways by bronchoalveolar lavage using the instant monoclonal antibodies caused apoptosis of those eosinophils, both in the presence and absence of a secondary, crosslinking antibody (FIG. 8).

The functional consequences of Siglec-8 crosslinking in human basophils and mast cells was also explored. Culture of human basophils under crosslinking conditions resulted in reductions in total cellular histamine content as well as IgE-dependent histamine release responses. Although apoptosis was not specifically studied in this preliminary experiment, the most likely explanation for the results observed is induction, by Siglec-8 crosslinking, of apoptosis and subsequent necrosis during culture, as well as reduced IgE-dependent releasability. In separate experiments, HMC-1 cells subjected to Siglec-8 crosslinking for 72 hours displayed enhanced apoptosis as determined by annexin-V staining (47% apoptosis compared to 26% apoptosis under control conditions, means of n=2). These data suggest that crosslinking of Siglec-8 may have profound consequences on mast cell and basophil function and survival.

What is claimed is:

1. A method for inducing apoptosis of a cell expressing SAF-2 comprising contacting the cell with a therapeutic agent that binds to SAF-2, wherein the therapeutic agent comprises an antibody that binds to an extracellular domain of SAF-2, wherein the antibody comprises immunoglobulin complementarity determining regions of the antibody are set forth in SEQ ID NOs: 5, 6, 7, 8, 9 and 10.

2. The method of claim 1 wherein the cell is selected from the group consisting of eosinophils, basophils and mast cells.

3. A method for treating a hypereosinophilic syndrome, the method comprising administering to a subject in need thereof an effective amount of a pharmaceutical composition comprising a therapeutic agent that binds SAF-2, wherein the therapeutic agent comprises an antibody that binds to an extracellular domain of SAF-2.

4. The method of claim 3, wherein the antibody comprises immunoglobulin complementarity determining regions set forth in SEQ ID NOs: 5, 6, 7, 8, 9 and 10.

5. The method of claim 3, wherein the antibody comprises a heavy chain variable region polypeptide as set forth in SEQ ID NO:2 and a kappa light chain variable region polypeptide as set forth in SEQ ID NO:4.

6. The method of claim 3, wherein the antibody comprises a heavy chain variable region polypeptide as set forth in SEQ ID NO:2.

7. The antibody method of claim 3, wherein the antibody comprises a kappa light chain variable region polypeptide as set forth in SEQ ID NO:4.

8. A method for inducing apoptosis of a cell expressing SAF-2 comprising contacting the cell with a therapeutic agent that binds to SAF-2, wherein the therapeutic agent comprises an antibody that binds to an extracellular domain of SAF-2, wherein the antibody comprises a heavy chain variable region polypeptide as set forth in SEQ ID NO:2.

9. The antibody method of claim 8, wherein the antibody comprises a heavy chain variable region polypeptide as set forth in SEQ ID NO:2 and a kappa light chain variable region polypeptide as set forth in SEQ ID NO:4.

10. A method for inducing apoptosis of a cell expressing SAF-2 comprising contacting the cell with a therapeutic agent that binds to SAF-2, wherein the therapeutic agent comprises an antibody that binds to an extracellular domain of SAF-2, wherein the antibody comprises a kappa light chain variable region polypeptide as set forth in SEQ ID NO:4.

* * * * *